US006350905B1

(12) United States Patent
Sharpless et al.

(10) Patent No.: US 6,350,905 B1
(45) Date of Patent: Feb. 26, 2002

(54) AMINOHYDROXYLATION OF OLEFINS

(75) Inventors: K. Barry Sharpless, La Jolla; Valery Fokin, Carlsbad, both of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/378,516

(22) Filed: Aug. 20, 1999

(51) Int. Cl.[7] ..................... C07C 299/04; C07C 303/00
(52) U.S. Cl. .................... 562/575; 549/76; 560/12; 560/27; 560/29; 560/115; 560/160; 562/553; 562/590
(58) Field of Search ................ 560/12, 27, 29, 560/115, 160; 562/575, 553, 590; 549/76

(56) References Cited

U.S. PATENT DOCUMENTS 5,767,304 A    6/1998  Sharpless et al.
5,859,281 A  * 1/1999  Sharpless et al. ............. 560/12
5,994,583 A  * 11/1999 Sharpless et al. ........... 562/575

OTHER PUBLICATIONS

Dress et al, Tetrahydron Lett., 39, pp 7669–7672, 1998.*
Sharpless, et al., "Osmium–Catalyzed Vicinal Oxyamination of Olefins by Chloramine–T", *J. Org. Chem. 41;* 177–179 (1976).
Herranz, et al., "Improvements in the Osmium–Catalyzed Oxyamination of Olefins by Chloramine–T", *J. Org. Chem.* 43; 2544–2548 (1978).
Bennani, et al., "Asymmetric Dihydroxylation (AD) of N,N–Dialkyl and N–Methoxy–N–Methoxy–N–Methyl α,β– and β,γ–Unsaturated Amides", *Tet. Lett. 54:* 2079–2082 (1993).
Li, et al., "Catalytic Asymmetric Aminohydroxylation (AA) of Olefins", *Angew, Chem. Int. Ed. Engl. 35:* 451–454 (1996).

Rudolph, et al., "Smaller Substituents on Nitrogen Facilitate the Osmium–Catalyzed Asymmetric Aminohydroxylation", *Angew. Chem. Int. Ed. Engl. 35:* 2810–2813 (1996).
Li, et al., "N–Halocarbanate Salts Lead to More Efficient Catalyic Asymmetric Aminohydroxylation", *Angew. Chem. Int. Ed. Engle. 35:* 2813–2817 (1996).
Bruncko, et al., "N–Bromoacetamide–A New Nitrogen Source for the Catalytic Asymmetric Aminohydroxlation of Olefins", *Angew. Chem. Int. Ed. Engl. 36:* 1483–1486 (1997).
Rubin, et al., "A Highly Efficient Aminohydroxylation Process", *Angew. Chem. Int. Ed. Engl. 36:* 2637–2640 (1997).
Reddy, et al., "N–Chloro–N–Sodio–2–Trimethylsilyl Ethyl Carbamate: A New Nitrogen Source for the Catalytic Asymmetric Aminohydroxylation", *Tet. Lett. 39:* 3667–3670 (1998).
Dress, et al., "Catalytic Aminohydroxylation Using Adenine–Derivatives as the Nitrogen Source", *Tet. Lett. 39:* 7669–7672 (1998).
O'Brien, "Sharpless Asymmetric Aminohydroxylation: Scope, Limitations, and Use in Synthesis", *Angew. Chem. Int. Ed. Engl. 38:* 326–329 (1999).
Goossen, et al., "Catalytic Asymmetric Aminohydroxylation with Amino–Substituted Heterocycles as Nitrogen Sources", *Angew. Chem. Int. Ed. Engl. 38:* 1080–1083 (1999).
Pringle, et al., "The Osmium–Catalyzed Aminohydroxylation of Baylis–Hillman Olefins", *Tet. Lett. 40:* 5151–5154 (1999).

*Primary Examiner*—Shailendra Kumar
(74) *Attorney, Agent, or Firm*—Donald G. Lewis

(57) ABSTRACT

Osmium-catalyzed aminohydroxylation reactions are accelerated and expanded in scope by the use of olefinic substrates having ionic groups, either anionic or cationic. The use of ionic groups on olefinic substrates also extends the aminohydroxylatable positions of unsaturations to include α,β, β,γ, and γ,δ positions, with respect to such ionic groups. A mechanism for the disclosed acceleration and extension is provided.

17 Claims, 5 Drawing Sheets

OTHER PUBLICATIONS

Shapless, et al., "A New Reaction. Stereospecific Vicinal Oxamination of Olefins by Alkyl Imido Osmium Compounds", *J. Am. Chem. Soc. 97:* 2305–2307 (1975).

Herranz, et al., "Osmium–Catalyzed Vicinal Oxyaminations of Olefins by N–Chloro–N–argentocarbamates", *J. Am. Chem. Soc. 100:* 3596–3598 (1978).

Kolb, H. C. and Sharpless, K. B., "Asymmetric Aminohydroxylation", in *Transition Metals for Organic Synthesis: Building Blocks and Fine Chemicals,* Beller, M.; Bolm, C., eds.: vol. 1; Wiley–VCH, New York, 1998, pp. 243–260.

\* cited by examiner

| Starting acid | Product | |
|---|---|---|
| 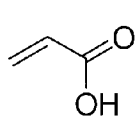 | 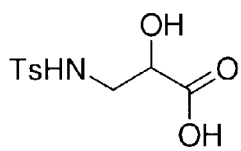 | 96% |
| 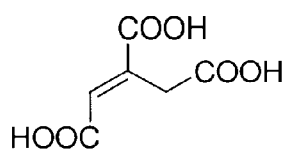 | 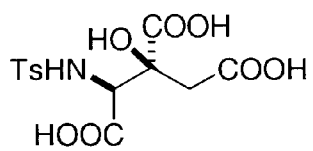 | 70% |
| 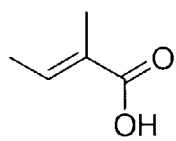 | 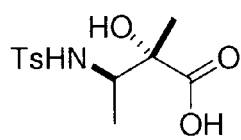 | 92% |
| 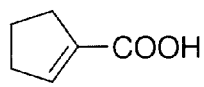 | 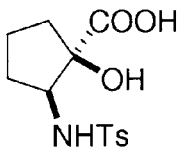 | 85% |
| 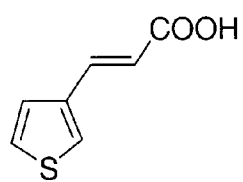 |  | 88% |
| 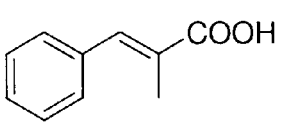 | 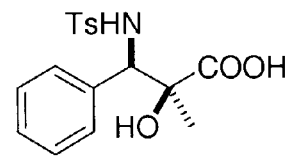 | 71% |
Figure 2

| Starting acid | Products (regioisomeric ratio of A:B) | | |
|---|---|---|---|
| | A | B | |
| HOOC-CH=CH-COOH | HOOC-CH(NHTs)-CH(OH)-COOH | | 90% |
| HOOC-CH=CH-COOEt | HOOC-CH(NHTs)-CH(OH)-COOEt | 1.6:1 + HOOC-CH(OH)-CH(NHTs)-COOEt | 88% |
| HOOC-CH=CH-COOH (cis) | HOOC-CH(OH)-CH(NHTs)-COOH | | 86% |
| HOOC-C(=CH₂)-CH₂-COOH | HOOC-CH₂-C(OH)(CH₂NHTs)-COOH | | 96% |
| HOOC-C(CH₃)=CH-COOH | HOOC-CH(OH)-C(CH₃)(NHTs)-COOH | | 71% |
| HOOC-CH=C(CH₃)-COOH | HOOC-CH(OH)-C(CH₃)(NHTs)-COOH | | 81% |
| HOOC-CH₂-CH=CH-COOH | HOOC-CH₂-CH(NHTs)-CH(OH)-COOH | 1.6:1 + HOOC-CH₂-CH(OH)-CH(NHTs)-COOH | 95% |

Figure 4

AMINOHYDROXYLATION OF OLEFINS

GOVERNMENT RIGHTS

This invention was made with government support under Grant No. GM-28384 awarded by the National Institutes of Health and with government support under Grant No. CHE-9531152 awarded by the National Science Foundation. The U.S. government has certain rights in the invention.

TECHNICAL FIELD

The present invention relates to the aminohydroxylation of olefins. More particularly, the present invention relates to an acceleration of the aminohydroxylation reaction by the use of olefinic substrates having ionic groups and to an expansion of the reaction to include the aminohydroxylation of olefins having a site of unsaturation at the α,β, β,γ, or γ,δ positions with respect to such ionic groups.

SUMMARY

Aminohydroxylation of ionic olefinic substrates is disclosed herein to be accelerated and/or have an expanded range as compared to nonionic olefinic substrates. Both anionic and cationic olefinic substrates are disclosed to be excellent substrates for the aminohydroxylation reaction. Also, it is disclosed herein, that, with the use of ionic olefinic substrates, the range of the reaction is expanded to include the aminohydroxylation of olefins having a site of unsaturation at the α,β, β,γ, or γ,δ positions with respect to polar ionic groups.

In the case of olefinic carboxylic acids, the aminohydroxylation reaction is disclosed to be rapid and nearly quantitative with very low catalyst loading in the absence of cinchona alkaloid ligands and with only one equivalent of the haloamine salt. The reactions can be conducted at molar concentrations in substrate, whereas the asymmetric aminohydroxylation (AA) process is best performed at 0.1 molar or less. A consequence of this "ligand-independent" reactivity is that the aminohydroxylation is not enantioselective, even in the presence of excess (e.g. 10 mol %) of the chiral ligand. This type of reactivity is referred to herein as "special A" below ("A" for "Aminohydroxylation").

The ready availability of the unsaturated acids from natural sources, the outstanding synthetic methods which lead to this functionality, and the importance of the α,β-hydroxyaminoacid derivatives obtained, make them one of the most attractive olefin classes yet found for the "special A" reaction. These substrates require the addition of base to neutralize the acid before the "special A" reactivity is observed. The base of choice is sodium bicarbonate, as it can be used in slight excess without impeding the rate of reaction, thus even further simplifying the experimental procedure. Of course, other bases can be successfully employed, provided that pH of the reaction mixture does not exceed ca. 11. A range of solvents can be employed for this reaction (water/acetonitrile, water/tert-butanol), but very importantly, the reaction often proceeds just as well in water without organic cosolvent. Exactly one equivalent of haloamine salt can be employed without compromising in aminohydroxylation of other substrates), and osmium catalyst loading is among the lowest known for the catalytic aminohydroxylations (0.1–1.0%, as opposed to the usual 4–5%). The only byproduct of the reaction is sodium chloride. Upon acidification, most products precipitate in pure form making chromatography or recrystallization unnecessary. In cases where regioisomers are possible, their separation is usually quite easy. For example, the α-toluenesulfonamido-β-hydroxy derivative of cinnamic acid is water soluble, whereas its regioisomer is not (Scheme 1).

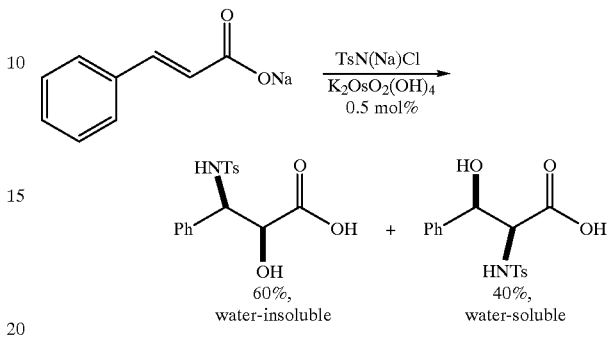

This newly discovered transformation is of wide scope and has been performed on large scale with fumaric acid, producing the aminohydroxylated product in almost quantitative yield (Scheme 2).

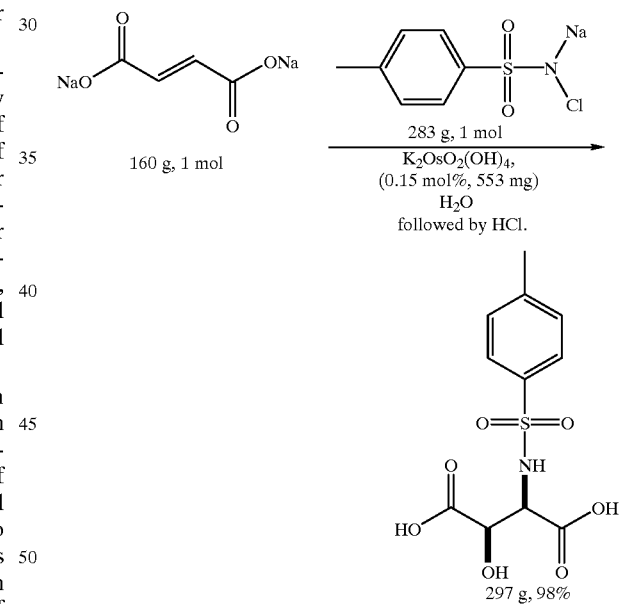

Another notable feature is that unlike other substrate classes, the reaction does not strictly require the "activating group" to be directly attached to the olefin for the enhanced reactivity effect. Thus, β,γ-unsaturated acids have also been found to aminohydroxylate readily (Scheme 3).

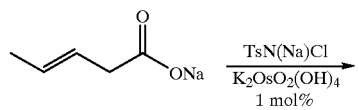

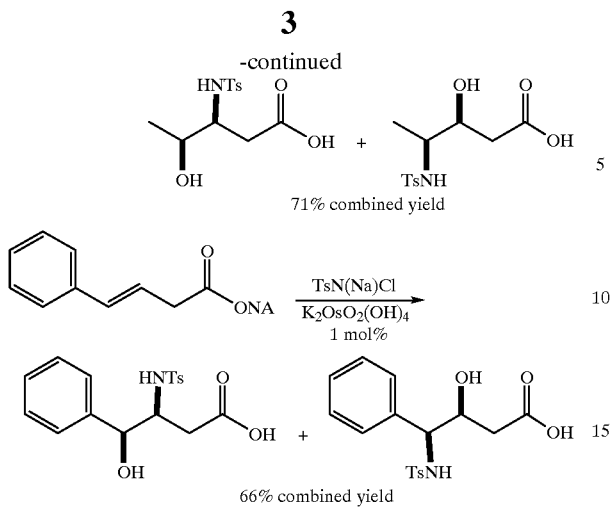

71% combined yield

66% combined yield

Thus, a class of olefins has been discovered which exhibits extraordinary reactivity in the catalytic aminohydroxylation process. The products are racemic, since tertiary amine ligands appear to play no role in the catalytic cycle. Nevertheless, the outstanding yields and practicality make these racemic variants important alternatives to the related AA transformations. The mechanistic implications of these observations are described in the next section.

Mechanistic Considerations.

An overall mechanistic pathway for aminohydroxylation is outlined below (Scheme 4). Osmium(VIII) trioxoimido species 1 can add to olefin to give the Os(VI) azaglycolate complex 2. This step is presumably strongly accelerated by the chiral ligand L, accounting for asymmetric induction in the process. Complex 2 can be hydrolyzed (not shown) or reoxidized to the central OS(VIII) azaglycolate 3. This species completes the "first cycle" by hydrolysis, or enters the "second cycle" by oxidizing another olefin to give bis(azaglycolate) complex 4. It is disclosed that the five-coordinate nature of 3 (in contrast to the four-coordinate 1) provides sufficient electron density at the metal center to allow olefin oxidation to proceed without external ligand. Indeed, chiral ligands such as those derived from DHQ and DHQD, even in five-fold excess relative to osmium, have no effect on the rate, yield, chemo-, regio- or stereochemical outcome of the reaction. In principle, the azaglycolate ligand resident on 3 can contribute to selectivity in this second olefin oxidation event.

Hydrolysis of 4 restores 2, completing the second cycle. The second cycle in dihydroxylation (in which the oxidant is an Os(VII) trioxo glycolate species) leads to low enantiomeric excess in the Upjohn process. This does not mean that a second cycle is necessarily deleterious to aminohydroxylation; indeed, we believe it to be the dominant catalytic mechanism for "special A" reactions, for the reasons outlined below. An important insight is that for aminohydroxylation reactions, hydrolysis is the turnover-limiting event in either catalytic cycle. This has been demonstrated in several ways, one example being the general observation that aminohydroxylation of a mixture of two olefins invariably proceeds at the same rate as the slower substrate alone. In these cases, the resting state of the osmium catalyst is the azaglycolate complex of the slowest substrate, with the overall reaction rate determined by the rate of its hydrolysis.

Scheme 4

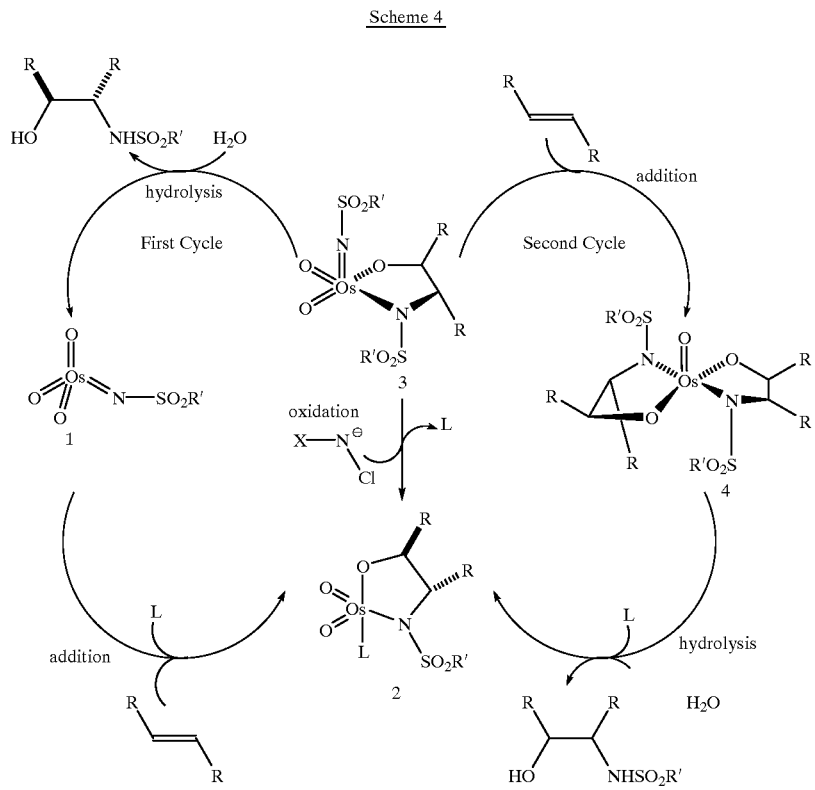

A structure representing the bis complex within the Second Cycle for the osmium catalysis of α,β unsaturated carboxylic acids is illustrated in FIG. 5. The complex has the expected square-pyramidal structure that is consistent with solution-phase NMR data. Note that, in comparison to the Os(VI) bis(glycolate) species that occupies the same position in the AD second cycle, complex 5 has much greater steric hindrance along the path by which water must approach the only open coordination site of osmium to initiate hydrolysis. The approach of water may also be slowed by the hydrophobic pocket created by the two tosyl groups that point "down" and around the vacant coordination site. These features are consistent with the observation that catalytic aminohydroxylation is generally slower than dihydroxylation, and with the hypothesis that hydrolysis is turnover-limiting.

Unsaturated carboxylic acids that exhibit "special A" reactivity (very high yields, no diol contamination, very low catalyst loadings, stoichiometric amounts of oxidant) seem to have overcome many of the problems that hindered the use of AA (Asymmetric Aminohydroxylation) except, of course, for enantioselectivity. The key feature among these olefins is that they all contain highly polar group(s) (e.g., carboxylates) near the double bond, thus providing a more hydrophilic environment in the vicinity of the open coordination site under the square pyramid of the Os(VI) bis(azaglycolate) complex, and/or near the apical oxo group on the other side. These are the two sites whose environment is disclosed herein to have the largest effect on the rates of the initial steps in ligand exchange/hydrolysis. A proximal carboxylate, for example, can directly facilitate hydrolysis of the complex as shown in Scheme 5 (a general structure of Os(VI) bis-azaglycolate complex obtained from an unsaturared acid is shown below).

(carboxylate). Thus, β,γ- and γ,δ-unsaturated acids also aminohydroxylate readily.

In addition to unsaturated carboxylic acids, it is disclosed herein that phosphonic acids, sulfonic acids, and other anionic and cationic substrates participate in this novel aminohydroxylation process, although with lower yields. It is disclosed that many other charged olefinic substrates containing either anionic [carboxylate, phosphonate, etc.] or cationic [quaternary ammonium] group(s) in close proximity to the double bond have this enhanced reactivity. All these highly polar hydrophilic groups facilitate hydrolysis (the rate-determining step) of the Os(VI)-bis(azaglycolate), the key intermediate in the catalytic cycle.

Accordingly, one aspect of the invention is directed to an improved process for catalyzing an aminohydroxylation of an unsaturation of an olefinic substrate by osmium catalysis. The aminohydroxylation reaction is accelerated by providing an ionic group on the olefinic substrate. The unsaturation of the olefinic substrate can be positioned α,β, β,γ, or γ,δ with respect to the ionic group. In a first preferred mode, the ionic group is an anion. Preferred anionic groups carboxylic acids, sulfonic acids, and phosphonic acids. A preferred nitrogen source is N-halo-N-sodiosulfonamide. Water is employed as a preferred solvent. The pH range should be within 6.5 to 10; however, a pH range of 7 to 10 is better; and a pH range within 8.5 to 9.5 is preferred. Preferred olefinic substrates include an aminohydoxylatable site of unsaturation at a position selected from the α,β, β,γ, and γ,δ positions with respect to the ionic group. In a second preferred mode, the ionic group is a cation. A preferred cationic group is quaternary ammonium. The same preferred pH ranges apply for both anionic and cationic substrates.

Scheme 5

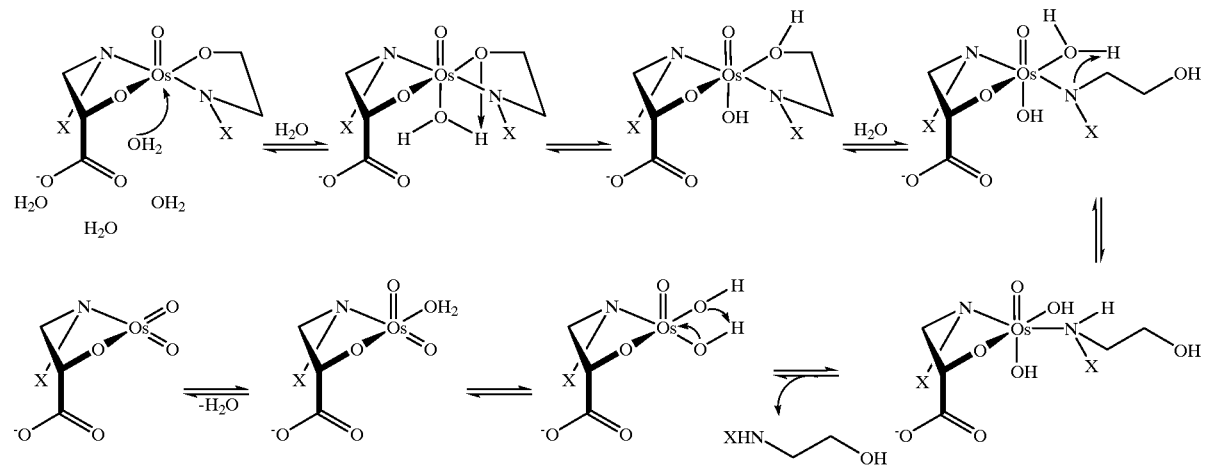

Ionic substrates, including carboxylic acids and other anionic and cationic substrates form a unique class of substrates process because they participate in Os-catalyzed aminohydroxylation with unprecedented turnover rates, very low catalyst loading, and, in many instances, give essentially pure products in very high yields. Use of these substrates results in a most efficient osmium-catalyzed process.

Another special feature of this process is that olefin does not have to be directly conjugated with the activating group FIG. 2 illustrates further examples of the aminohydroxylation of carboxylic acids.

Figure 1:
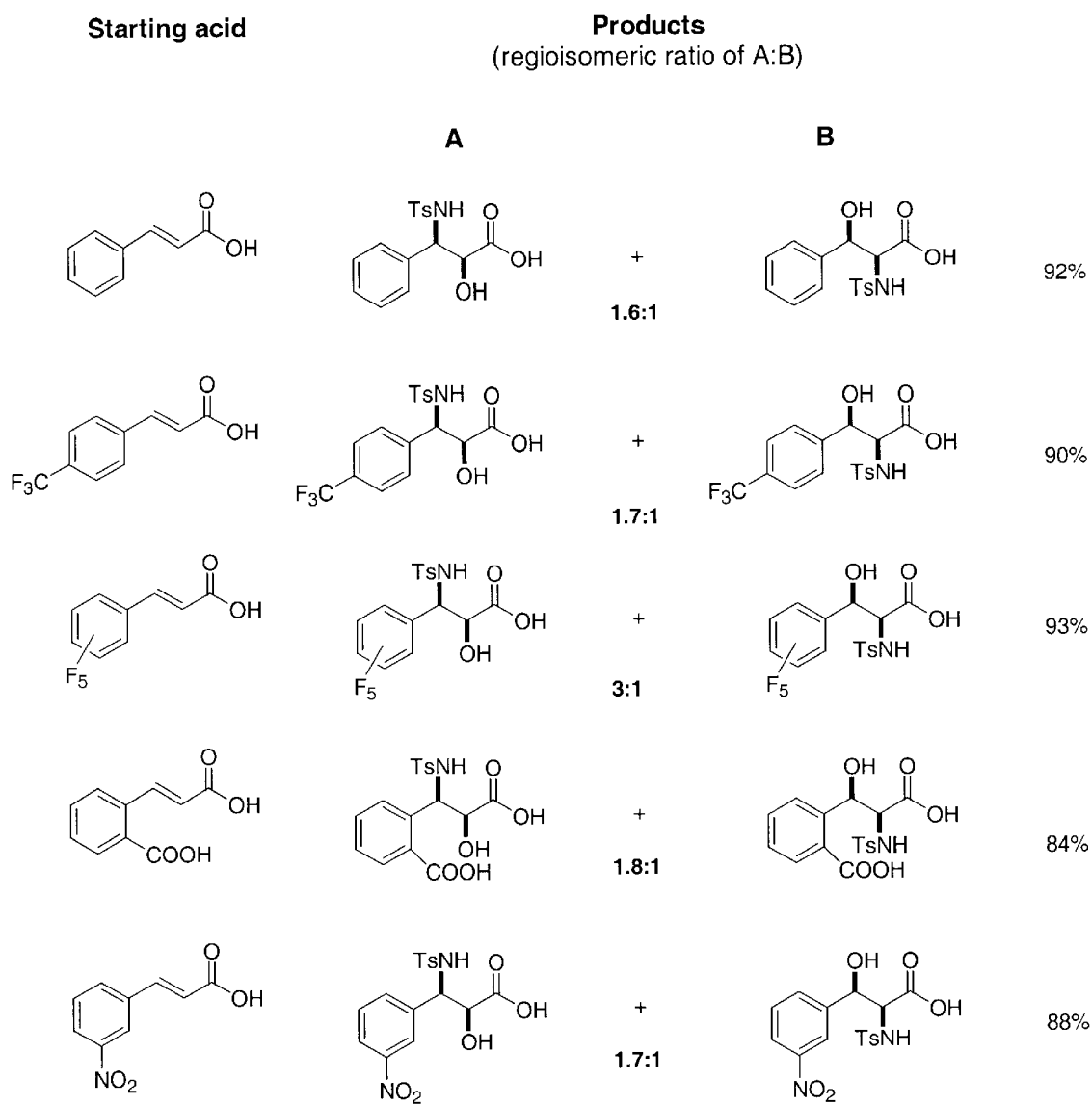
FIG. 1 illustrates examples of the aminohydroxylation of carboxylic acids.
Figure 3:
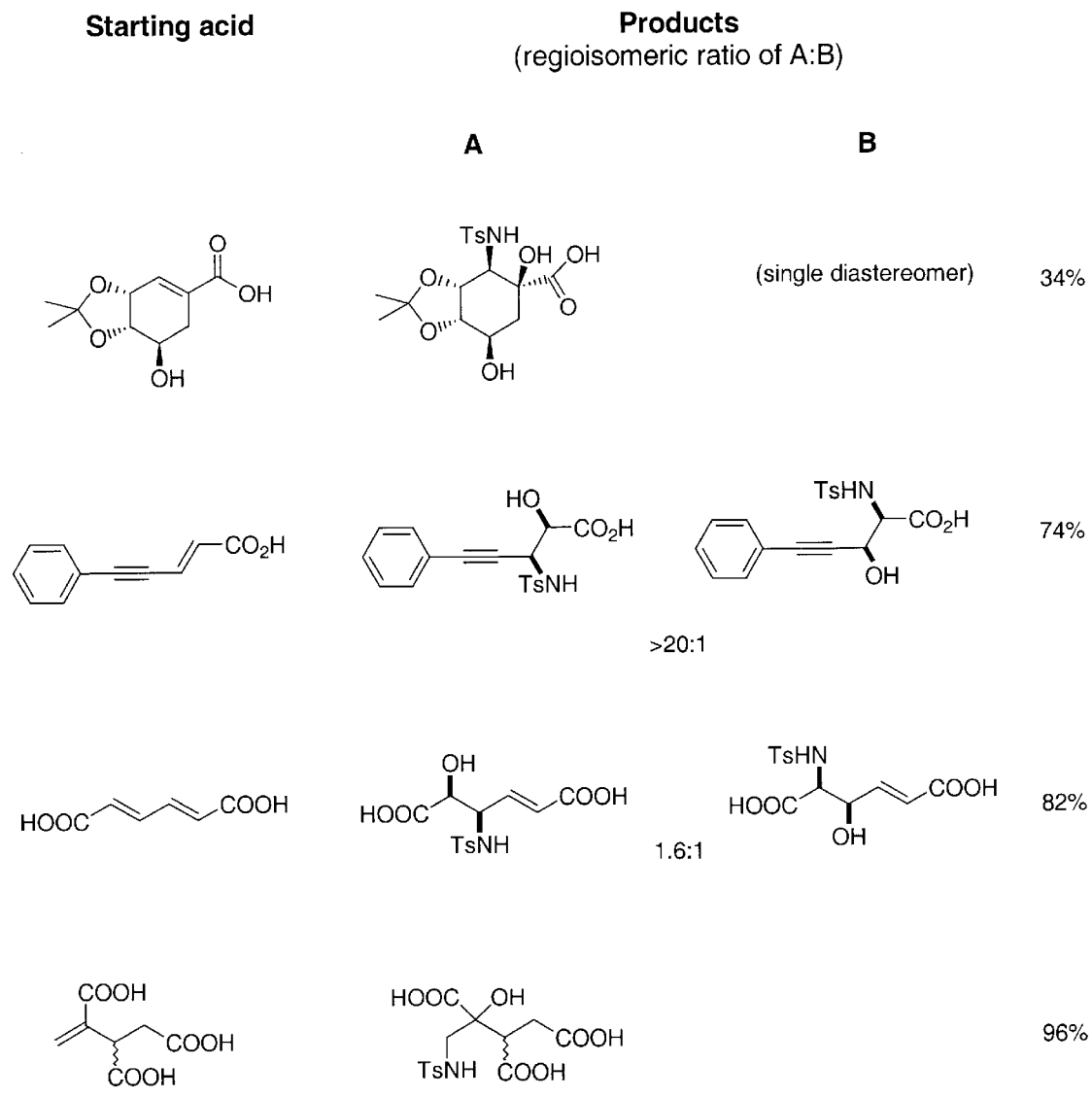

FIG. 3 illustrates further examples of the aminohydroxylation of carboxylic acids.

FIG. 4 illustrates further examples of the aminohydroxylation of carboxylic acids.

Figure 5:
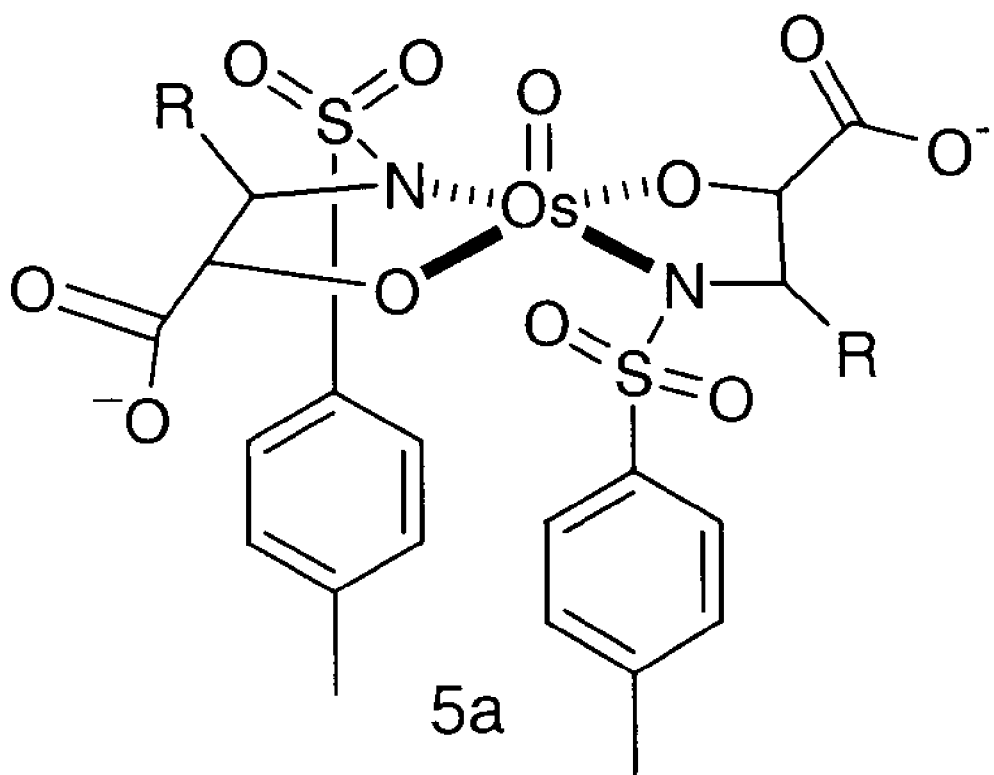

FIG. 5 illustrates the structure of the bis complex of the "second cycle" of the osmium catalyzed aminohydroxylation of olefinic carboxylic acids.

DETAILED DESCRIPTION

Alkali metal salts of α,β-unsaturated carboxylic acids are converted to their corresponding α,β-hydroxysulfonamide derivatives by treatment with N-halo-N-sodiosulfonamides in the presence of catalytic amounts of osmium (VIII) oxide or potassium osmate (VI) dihydrate. The reaction is experimentally simple, proceeds in high yields in a variety of solvents, including water, tert-butanol, and acetonitrile, and produces virtually no byproducts (NaCl is the only byproduct produced).

Scheme 6

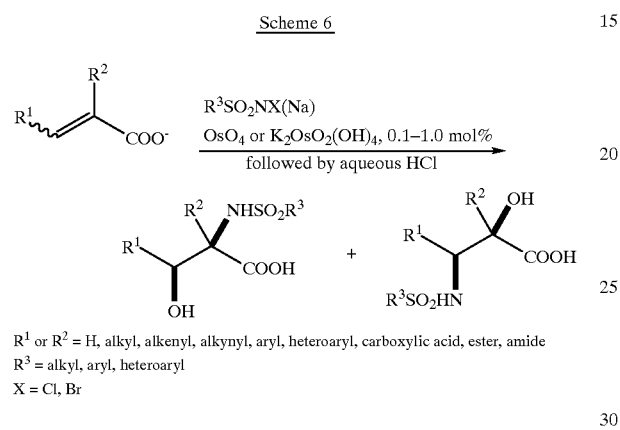

$R^1$ or $R^2$ = H, alkyl, alkenyl, alkynyl, aryl, heteroaryl, carboxylic acid, ester, amide
$R^3$ = alkyl, aryl, heteroaryl
X = Cl, Br General Experimental Procedure:

An acid (10 mmol) and sodium bicarbonate (11 mmol, 1.1 eq per carboxylic acid group) were dissolved in 25 mL of solvent (1:1 tert-butanol/water, acetonitrile/water, or water). After gas evolution ceased, Chloramine-T (10 mmol) was added, followed by catalyst ($K_2OsO_4$, 0.1–1.0 mol %). The reaction was stirred at room temperature for 6–24 hrs. It was then quenched with 0.2 mmol of sodium sulfite and stirred for an additional hour. It was then cooled down in an ice bath, 75 mL of water was added, followed formed was filtered, washed with cold water, and dried to afford essentially pure product (>95% purity in most cases).

EXAMPLES

Aminohydroxylation of the Fumaric Acid on 1 mol Scale (Scheme 7):

Fumaric acid (1) (116 g, 1 mol) and sodium bicarbonate (186 g, 2.2 mol) were dissolved in 1.5 L of water in a 3 L Erlenmeyer flask. After gas evolution ceased, Chloramine-T trihydrate (281 g, 1 mol) was added, followed by potassium osmate (735 mg, 0.2 mol %). The reaction turned dark brown and was left stirring for 8 hours, at which time it cleared and turned light green. No oxidizing agent could be detected at this point (starch/iodide test). Sodium sulfite (500 mg) was added, and reaction was stirred for an additional hour. 500 mL of 5M HCl was then added, and the mixture was left in a refrigerator overnight. The crystals that formed were filtered, washed with a small amount of ice-cold water, and dried to yield 280 g (92%) of pure product (2).

Scheme 7

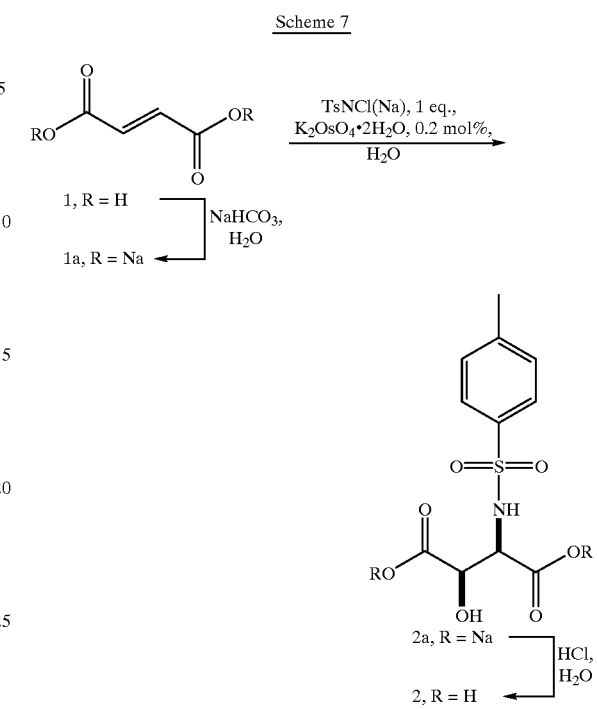

Aminohydroxylation of the Cinnamic Acid (Scheme 8):

Cinnamic acid (3) (7.4 g, 50 mmol) and sodium bicarbonate (4.7 g, 55 mmol) were stirred in 200 mL of water. After all the solids dissolved and gas evolution ceased, Chloramine-T trihydrate (14.1 g, 50 mmol) was added, followed by potassium osmate dihydrate (184 mg). The reaction turned dark brown and was left stirring at room temperature for 12 hrs. HPLC analysis revealed complete consumption of the starting materials. Sodium sulfite (250 mg) was added, and the reaction was stirred for an additional hour. It was then cooled to 0° C. in a water/ice bath and 2M HCl (50 mL) was added with vigorous stirring. The precipitate formed was filtered, washed with water until it was white (ca. 300 mL), and dried to afford 9.7 g of the regioisomer (4). The filtrates were combined and placed in a refrigerator for 24 hrs. Precipitate formed was filtered, washed with a small amount of ice-cold water, and dried to afford 5.1 g of the regioisomer (5). Combined yield 92.5%.

Scheme 8

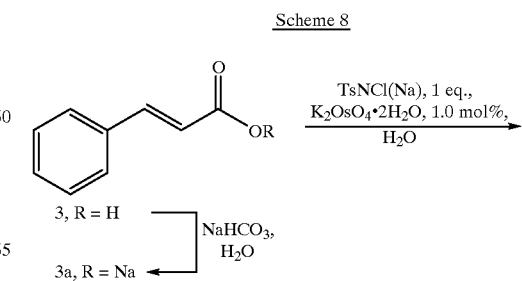

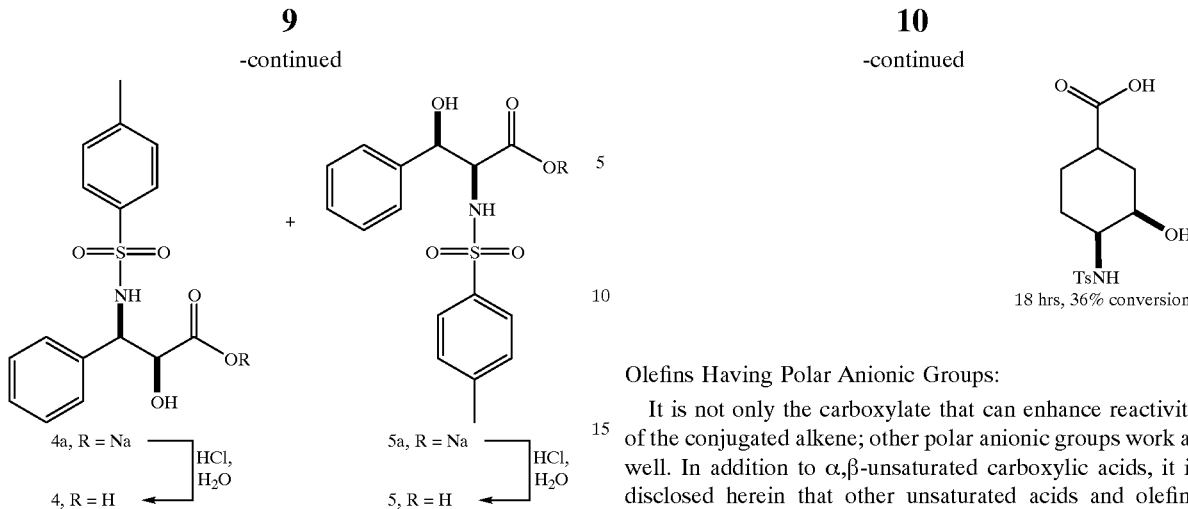

4a, R = Na  
4, R = H  ⇌ HCl, H₂O

5a, R = Na  
5, R = H  ⇌ HCl, H₂O 18 hrs, 36% conversion

Other examples of α,β-unsaturated carboxylic acids are listed in FIGS. 1–4. Examples of aminohydroxylations of olefinic carboxylic acids having unsaturations at the β,γ and γ,δ positions are provided below.

Aminohydroxylation of Trans-3-pentenoic Acid:

The reaction was conducted in water as the solvent according to the general procedure. 1 mol % of the Os catalyst was used. The solution was stirred for 18 hrs at room temperature. Products were isolated as a mixture of regioisomers by acidification with HCl, cooling down in an ice-water bath and filtration. Physical data: MS (ES+, CH$_3$CN/H$_2$O, 1:1. Calculated for C$_{12}$H$_{17}$NO$_5$S 287, found 288 ([M+H]$^+$), 310 ([M+Na]$^+$)).

Aminohydroxylation of Trans-styrylacetic Acid (4-phenyl-3-butenoic acid):

The reaction was conducted similarly to the trans-3-pentenoic acid reaction above. Physical data: MS (ES+, CH$_3$CN/H$_2$O, 1:1. Calculated for C$_{17}$H$_{19}$NO$_5$S 349, found 372 ([M+Na]$^+$)).

Aminohydroxylation of 3-cyclohexenecarboxylic Acid (Scheme 9):

The reaction was conducted in water as the solvent according to the general procedure. 1 mol % of the Os catalyst was used. This solution was stirred for 18 hrs at room temperature. The resulting products were isolated as a mixture of regioisomers by acidification with HCl and extraction with diethyl ether/methanol (95:5). Physical data: MS (ES+, CH$_3$CN/H$_2$O, 1:1. Calculated for C$_{14}$H$_{19}$NO$_5$S 313, found 314 ([M+H]$^+$), 336 ([M+Na]$^+$)).

Scheme 9

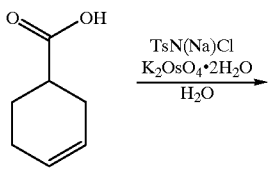

TsN(Na)Cl  
K$_2$OsO$_4$·2H$_2$O  
———————→  
H$_2$O

Olefins Having Polar Anionic Groups:

It is not only the carboxylate that can enhance reactivity of the conjugated alkene; other polar anionic groups work as well. In addition to α,β-unsaturated carboxylic acids, it is disclosed herein that other unsaturated acids and olefins having polar anionic groups can participate in this transformation to the aminohydroxylate. Exemplary unsaturated acids and olefins having polar anionic groups include vinylphosphonic and vinylsulfonic acids. However, the conversion/yields of these classes of compounds are often not as high as for the carboxylic acids. This is a whole new type of reactivity that has been uncovered.

Aminohydroxylation of Vinylphosphonic Acid (Scheme 10):

The reaction was conducted in water as the solvent on 5 mmol scale, 2.2 equivalents (11 mmol) of sodium bicarbonate were used to neutralize the acid; 2 mol % of Os catalyst was used. The reaction was run for 18 hrs and was monitored by LC/MS. The product was isolated by extraction (ethyl acetate/methanol, 95:5) after quenching with sodium sulfite (0.5 mL of 1M solution) and acidification with 1M HCl. Physical data: MS (ES+, CH$_3$CN/H$_2$O, 1:1. Calculated for C$_9$H$_{14}$NO$_6$PS 295, found 296 ([M+H]$^+$), 318 ([M+Na]$^+$)).

Scheme 10

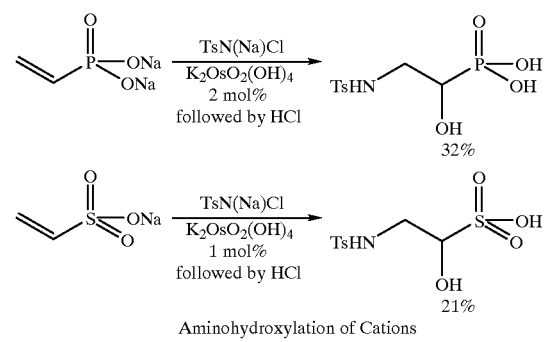

Aminohydroxylation of Cations

Aminohydroxylation of Vinylsulfonic Acid Sodium Salt (Scheme 10):

Commercially available (Aldrich) solution of the vinylsulfonic acid sodium salt was subjected to aminohydroxylation in water with 2.0 mol % of Os catalyst. The reaction was run for 18 hrs and was monitored by LC/MS. The product was isolated by extraction (ethyl acetate/methanol, 95:5) after quenching with sodium sulfite (0.5 mL of 1M solution) and acidification with 1M HCl. Physical data: MS (ES+, CH$_3$CN/H$_2$O, 1:1. Calculated for C$_9$H$_{13}$NO$_6$S$_2$ 295, found 296 ([M+H]$^+$), 318 ([M+Na]$^+$)). See scheme 10 above.

Scheme 11

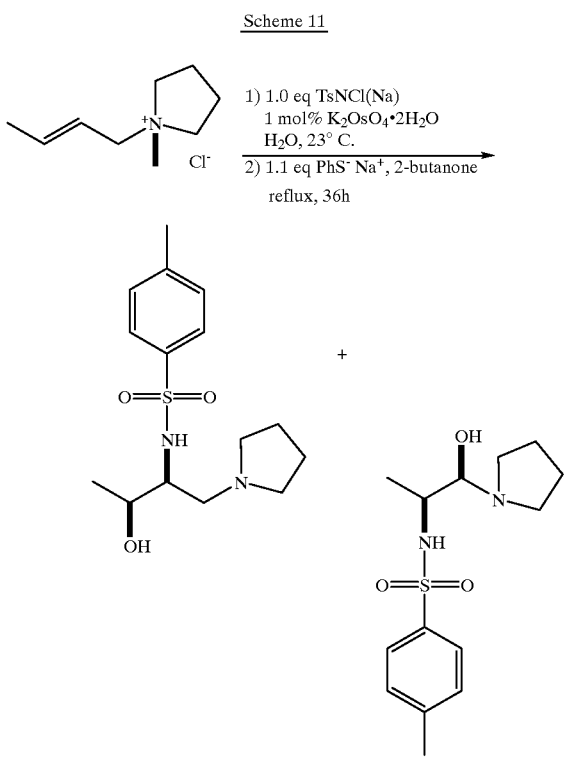

Aminohydroxylation of the N-(2Z)-Butenyl-N-methylpyrrolidinium Chloride (Scheme 11):

The N-(2Z)-butenyl-N-methylpyrrolidinium chloride (8.9 g, 50 mmol) is stirred in 200 mL of water. After all the solids dissolved, Chloramine-T trihydrate (14.1 g, 50 mmol) is added, followed by potassium osmate dihydrate (184 mg, 1 mol %). The reaction turns dark brown and is left stirring at room temperature for 12 hrs. HPLC analysis reveals complete consumption of the starting materials. Sodium sulfite (250 mg) is added, and the reaction is stirred for an additional hour. The water is evaporated off under reduced pressure to leave the brownish-tan salt residue. The residue is dissolved in refluxing 2-butanone and sodium thiophenoxide (7.26 g, 55 mmol) is added. This mixture is refluxed until the ammonium salt is consumed or for no longer than 36 hours. The majority of the 2-butanone is distilled off and the residue is partitioned between water and diethyl ether. The aqueous layer is extracted with diethyl ether (2×100 ml) and the combined organic layers are washed with saturated sodium carbonate (100 mL) and brine (50 mL). Column chromatography affords the N-tosyl-protected diaminoalcohols as separate regioisomers.

Starting Materials and Reagents:

Most unsaturated acids are available commercially and were purchased from Aldrich, Acros, and Lancaster chemical companies.

General Procedure for the Preparation of Chloramine Salts of Sulfonamides:

Some N-halo-N-sodiosulfonamides (chloramine salts of sulfonamides) are available commercially (such as Chloramine-T, Chloramine-B). Others are prepared from commercially available sulfonamides or sulfonamides prepared from commercially available sulfonyl chlorides.

First Method:

To a stirred solution of a sulfonamide (100 mmol) and sodium hydroxide (100 mmol) in 100 ml of water was slowly added t-BuOCl (100 mmol). The solution was stirred for 1 hr and concentrated to dryness in vacuo. After one trituration with diethyl ether pure salt was obtained. Chloramine salt can also be generated in situ; in that case, it is not isolated but used directly as a solution for the aminohydroxylation.

Second Method:

To a stirred solution of a sulfonamide (100 mmol) and potassium carbonate (50 mmol) in 200 mL of 1:1 mixture of acetonitrile/water was added 1,3-dibromo-5,5-dimethylhydantoin (50 mmol). The solution was stirred for 15 min and used directly in the subsequent aminohydroxylation. The advantage of this procedure is that both reagents are stable solids which are available commercially.

Figure 12

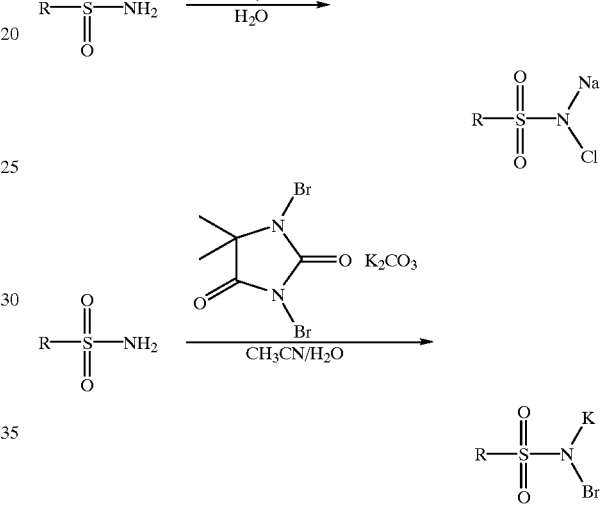

D,L-threo-N-(p-toluenesulfonamido)-β-hydroxyaspartic Acid:

D,L-threo-N-(p-toluenesulfonamido)-β-hydroxyaspartic acid was prepared in 98% yield according to the general procedure using water as a solvent. After acidification, solution was placed in a refrigerator for 24 hrs. Crystals formed were collected by filtration. Physical data: m. p. 188–191° C. (dec.); $^1$H NMR (DMSO-$d_6$, 500 MHz). δ: 7.65 (d, J=7.8 Hz, 2H), 7.29 (d, J=7.8 Hz, 2H), 4.05 (d, J=3.4 Hz, 1H), 3.88 (d, J=3.4 Hz, 1 H), 2.33 (s, 3H); $^{13}$C NMR (DMSO-$d_6$, 125 MHz). δ: 173.93, 171.29, 142.26, 138.33, 129.27, 126.78, 71.63, 58.84, 21.03.

D,L-threo-N-(p-nitrobenzenesulfonamido)-β-hydroxyaspartic acid:

D,L-threo-N-(p-nitrobenzenesulfonamido)-β-hydroxyaspartic acid was prepared in 88% yield according to the general procedure using 1:1 acetonitrile/water as a solvent and p-nitrobenzenesulfonamide brominated in situ with 1,3-dibromo-5,5-dimethylhydantoin. After acidification, solution was placed in a refrigerator for 24 hrs. Crystals formed were collected by filtration. Physical data: m. p. 151–153° C. (dec.); $^1$H NMR (DMSO-$d_6$, 500 MHz). δ: 8.31 (d, J=8.8 Hz, 2H), 8.01 (d, J=8.8 Hz, 2H), 4.24 (d, J=3.4 Hz, 1H), 4.16 (d, J=3.4 Hz, 1 H); $^{13}$C NMR (DMSO-$d_6$, 125 MHz). δ: 172.98, 170.61, 149.29, 147.26, 128.30, 124.04, 71.25, 59.21.

D,L-threo-2-hydroxy-3-(p-toluenesulfonamido)-3-phenylpropionic Acid and D,L-threo-3-hydroxy-2-(p-toluenesulfonamido)-3-phenylpropionic Acid:

D,L-threo-2-hydroxy-3-(p-toluenesulfonamido)-3-phenylpropionic acid and D,L-threo-3-hydroxy-2-(p-toluenesulfonamido)-3-phenylpropionic acid were prepared in 92% combined yield according to the general procedure using 1:1 tert-butanol/water as a solvent. Regioisomeric ratio was determined to be 1.6:1.

The first regioisomer precipitated from the reaction mixture upon acidification. After washing with water, the crystals were dried and analyzed. Physical data: m. p. 216–219° C. (dec.); $^1$H NMR (DMSO-d$_6$, 500 MHz). δ: 8.10 (d, J=9.6 Hz, 1H), 7.37 (d, J=8.3 Hz, 2H), 7.10–7.03 (m, 7H), 4.73 (dd, J=9.6 and 3.1 Hz, 1H), 4.05 (d, J=3.1 Hz, 1H), 2.22 (s, 3H); $^{13}$C NMR (DMSO-d$_6$, 125 MHz). δ: 172.87, 141.75, 138.67, 138.43, 128.78, 127.48, 126.66, 126.39, 74.36, 60.06, 20.87.

All filtrates were combined and placed in a refrigerator for 24 hrs to yield the second regioisomer which was collected by filtration. Physical data: m. p. 184–186° C. (dec.); 1H NMR (DMSO-d$_6$, 500 MHz). δ: 7.63 (d, J=9.3 Hz, 1H), 7.35 (d, J=7.9 Hz, 2H), 7.26 (m, 2H), 7.20–7.15 (m, 5H), 4.96 (d, J=3.7 Hz, 1H), 3.91 (dd, J=9.3 and 3.7 Hz, 1H), 2.31 (s, 3H); $^{13}$C NMR (DMSO-d$_6$, 125). δ: 170.98, 143.93, 141.89, 141.44, 138.37, 129.02, 127.64, 126.38, 126.28, 72.78, 62.26, 20.93.

What is claimed is:

1. An improved process for catalyzing an aminohydroxylation of an unsaturation of an olefinic substrate by osmium catalysis, wherein the improvement comprises:

accelerating the catalysis of said aminohydroxylation by providing an ionic group on the olefinic substrate, the unsaturation of the olefinic substrate being positioned α,β, β,γ, or γ,δ with respect to the ionic group.

2. An improved process according to claim 1 wherein the ionic group is an anion.

3. An improved process according to claim 2 wherein the anion is selected from the group consisting of carboxylic acids, sulfonic acids, and phosphonic acids.

4. An improved process according to claim 2 wherein N-halo-N-sodiosulfonamide is employed as a nitrogen source and water is employed as a solvent having a pH within a range of 6.5 to 10.

5. An improved process according to claim 4 wherein the pH is within a range of 7 to 10.

6. An improved process according to claim 4 wherein the pH is within a range of 8.5 to 9.5.

7. An improved process according to claim 2 wherein the site of unsaturation of the olefinic substrate is at the α,β position with respect to the anionic group.

8. An improved process according to claim 2 wherein the site of unsaturation of the olefinic substrate is at the β,γ position with respect to the anionic group.

9. An improved process according to claim 2 wherein the site of unsaturation of the olefinic substrate is at the γ,δ position with respect to the anionic group.

10. An improved process according to claim 1 wherein the ionic group is a cation.

11. An improved process according to claim 10 wherein the cation is a quaternary ammonium.

12. An improved process according to claim 10 wherein N-halo-N-sodiosulfonamide is employed as a nitrogen source and water is employed as a solvent solvent having a pH within a range of 6.5 to 10.

13. An improved process according to claim 10 wherein the pH is within a range of 7 to 10.

14. An improved process according to claim 10 wherein the pH is within a range of 8.5 to 9.5.

15. An improved process according to claim 10 wherein the site of unsaturation of the olefinic substrate is at the α,β position with respect to the cationic group.

16. An improved process according to claim 10 wherein the site of unsaturation of the olefinic substrate is at the β,γ position with respect to the cationic group.

17. An improved process according to claim 10 wherein the site of unsaturation of the olefinic substrate is at the γ,δ position with respect to the cationic group.

* * * * *